United States Patent
Signorino

(10) Patent No.: US 6,620,431 B1
(45) Date of Patent: Sep. 16, 2003

(54) SHELLAC FILM COATINGS PROVIDING RELEASE AT SELECTED PH AND METHOD

(76) Inventor: Charles Signorino, 432 Joseph St., Norristown, PA (US) 19403

( * ) Notice: Subject to any disclaimer, the term of this patent is extended or adjusted under 35 U.S.C. 154(b) by 62 days.

(21) Appl. No.: 09/721,692

(22) Filed: Nov. 24, 2000

Related U.S. Application Data

(60) Provisional application No. 60/198,091, filed on Apr. 17, 2000.

(51) Int. Cl.$^7$ .............................. A61K 9/48; A61K 9/52; A61K 9/54; A61K 9/56; A61K 9/58

(52) U.S. Cl. ..................... 424/451; 424/457; 424/458; 424/459; 424/462; 424/468; 424/474; 424/475; 424/476; 424/482; 424/490; 424/497; 424/501

(58) Field of Search ............................. 424/451, 457, 424/458, 459, 462, 468, 474, 475, 476, 482, 490, 497, 501

(56) References Cited

U.S. PATENT DOCUMENTS

| | | | | |
|---|---|---|---|---|
| 3,477,864 A | * | 11/1969 | Tuji | 106/151 |
| 3,738,952 A | | 6/1973 | Signorino | 260/27 R |
| 3,741,795 A | * | 6/1973 | Signorino | 424/481 |
| 3,802,896 A | * | 4/1974 | Westall et al. | 106/140.1 |
| 4,146,533 A | | 3/1979 | Simon | 260/97 |
| 4,503,030 A | * | 3/1985 | Edgren et al. | 424/473 |
| 4,863,744 A | | 9/1989 | Urquhart et al. | 424/484 |
| 4,990,341 A | | 2/1991 | Goldie et al. | 424/484 |
| 5,194,464 A | * | 3/1993 | Itoh et al. | 106/170.21 |
| 5,425,950 A | | 6/1995 | Dandiker et al. | 424/480 |
| 5,525,634 A | | 6/1996 | Sintov et al. | 514/777 |
| 5,567,438 A | * | 10/1996 | Cook | 424/474 |
| 5,955,104 A | | 9/1999 | Momberger et al. | 424/458 |
| 5,980,951 A | | 11/1999 | Gardner et al. | 424/490 |

FOREIGN PATENT DOCUMENTS

| WO | WO 99/01121 | * | 1/1999 | |
|---|---|---|---|---|

OTHER PUBLICATIONS

The US Pharmacopeia/National Formulary NF 18 1995.*
Martin, J. "Shellac" Kirk Othmer Encyclopedia of Chemical Technology, 3$^{rd}$ Ed, p. 737 1982.*
National Formulary, NF 19, p. 2512.
X Li, RC Vasavada. "Shellac." Handbook of Pharmaceutical Excipients, 3rd Ed., 1999; p. 462.
National Formulary, NF 18, p. 2298.
Martin, James. "Shellac." Kirk Othmer Encyclopedia of Chemical Technology, 3rd Ed., 1982; p. 737.
Class, Jay B. "Natural Resins." Kirk Othmer Encyclopedia of Chemical Technology, vol. 21, 1997; p. 299.
Maiti, Sukumar and Md. Safikur Rahman. "Application of Shellac in Polymers." Journal of Macromolecular Science, vol. 26 Issue C. Review of Macromolecular Chemistry Physics. 1986 by Marcel Dekker; pp. 441–481.

* cited by examiner

Primary Examiner—Thurman K. Page
Assistant Examiner—Todd D Ware
(74) Attorney, Agent, or Firm—Michael F. Petock, Esq.

(57) ABSTRACT

Film coatings for enteric and colonic release at selected pH are provided by selecting and/or formulating a shellac of a predetermined acid number. The method includes the selection of the acid number to provide the release at the specified pH and a method of providing a shellac of a predetermined acid number by blending of shellacs of different acid numbers. In general, films that release or dissolve at or above pH 7.4 are based on the selection of shellac with an acid number below 74. Films that release or dissolve above pH 7.0 are comprised of shellac selected with an acid number below 80. Films that release or dissolve at below pH 7.0 are comprised of shellac selected to have an acid number above 80. The film coating may be modified with a water soluble resin and/or a plasticizer. Preferably the shellac will comprise 50% or more of the resin system, and is formed out of water, not alcohol.

7 Claims, No Drawings

SHELLAC FILM COATINGS PROVIDING RELEASE AT SELECTED PH AND METHOD

CROSS REFERENCES TO RELATED APPLICATIONS AND PATENTS

This application claims the benefit of U.S. Provisional Application No. 60/198/091, filed Apr. 17, 2000.

BACKGROUND OF THE INVENTION

It is well known in the art that shellac is an excellent film former. Shellac has been used for tablet coating for a century. Shellac films give good performance when freshly deposited out of alcohol but they crosslink and esterify in the dried film and extend the release characteristics after six months or a year. This particular defect has led to reduction in the use of shellac for tablet coating. The FDA lists the excipients used in NDA products every four years, in 1988 shellac was used in 278 listings, in 1992, 219, in 1996 it was used in only 73 listings. Because of the problems with shellac its use has been declining for more than 30 years. Many patents and other references note shellac, but it is not promoted but only mentioned as a known and historically used material. The pharmaceutical industry has moved away from shellac as a significant resin for coating. Forty years ago it was the most popular resin for enteric coating; today it is hardly used. The invention herein discloses surprising and new methods to make shellac very useful again.

SUMMARY OF THE INVENTION

Many attempts have been made to overcome these defects but the best modification of shellac systems is to use shellac out of water instead of alcohol. Shellac is very soluble in alcohol and can be used in old conventional pans for coating. However shellac holds on to the last traces of alcohol as the film dries. Using erased shellac eliminates these traces of alcohol and prevents esterification of the shellac. Other additives can be added to prevent crosslinking and make shellac useful for tablet coating.

The growth of the food supplement industry has presented a new opportunity for shellac since it is a food approved resin. There is an interest in using shellac for the numerous needs the food supplement industry has for reliable coating systems. Films that can give delayed release, enteric release and colonic release are in great demand. Coating is also needed for sealing products and taste masking many of the products as well. There is no other resin that is so versatile as shellac. Many of the resins used in drug manufacturing can not be used for food supplement products.

Briefly and basically, in accordance with the present invention, a film coating and a method of making a film coating are disclosed that produce a controlled release profile in an environment having a selected pH based on the shellac of a preselected acid number.

In accordance with the present invention, films that release or dissolve at or above pH 7.4 are based on the selection of shellac with an acid number below 74. Films that release or dissolve above pH 7.0 are comprised of a shellac selected with an acid number below 80. Films that release or dissolve at below pH 7.0 are comprised of shellac selected to have an acid number above 80.

The film may be modified with a water soluble resin at from 5–50% by weight of the shellac content while still giving the same pH release profile. Presently preferred water soluble resins may be selected from the group consisting of hydroxypropyl methylcellulose (HPMC), methylcellulose (MC), hydroxypropylcellulose (HPC), polyvinyl pyrrolidone (PVP), modified starch or maltodextrin and natural gums such as acacia.

The film may be plasticized with the fatty acids at from about 10–20% by weight of the combined resin content and from about 5–20% by weight of a water soluble plasticizer to enhance the release profile of the film. The fatty acids may be oleic acid, stearic acid or other fatty acids. Oleic acid is presently preferred. The water soluble plasticizer may preferably be selected from the group consisting of glycerine, propylene glycol, polyethylene glycol (molecular weight 300–8000), triacetin (TA) and triethyl citrate.

Preferably, the shellac will comprise 50% or more of the resin system.

The invention further includes the method of producing a film coating having a controlled release profile such that it will release in an environment having a specified pH using the method of selecting a shellac having a predetermined acid value. The method includes adding water soluble resins and plasticizers and dyes and other colorants. The method further includes the method of producing a shellac having a predetermined acid value by using the step of blending shellacs of known different acid values to produce a shellac having an acid value of a predetermined value. The shellac is preferably deposited out of water, and not alcohol.

DETAILED DESCRIPTION OF THE PREFERRED EMBODIMENTS

The present invention presents a method of using shellac that overcomes the defects and produces films that are useful and reliable. Several forms of shellac are available. Our interest will be directed to shellacs that are refined decolorized orange shellac with an acid number 68–73 and refined dewaxed bleached shellac with acid numbers 72–91. The shellacs of interest must meet the specification in the NF19. The acid number which is used in this disclosure is the acid value defined in the monograph and is mg. of KOH per gram of shellac. Formulating with shellac according to the acid number and the unique properties related to it will be the focus.

All the grades of shellac are compatible and can be blended to give resins of distinct acid number. We have found that shellac blends with acid numbers that are low dissolve in an environment having a high pH and those with high acid numbers dissolve in an environment having a low pH. Shellac with acid numbers 68–73 dissolves at pH above 7.4. Shellac with acid numbers 74–80 dissolves at pH 7 and above. Shellac with acid numbers above 80 dissolves at pH less than 7.

Shellac is dissolved in water with the aid of ammonium carbonate, ammonium bicarbonate or ammonia at about 50–60° C. The final solution will be clear at a pH above 7 and 10–30% solids of shellac. Shellac solids of known acid number are blended to give a desired acid number to the dissolved material. Alternatively shellacs of various acid number can be individually dissolved and the solutions blended to give the desired acid number to the mix.

With the shellac solutions as a starting base, formulations can be made for coating systems that meet any need for tablet coating, particle coating or encapsulation that is presented. The shellac coating of the present invention may be utilized in any type of pharmaceutical application including pellets, granules, tablets, capsules or any other pharmaceutical solid dosage form. Additionally, the shellac coating of the present invention may be utilized to coat various food supplements and other nutritional compositions. including, but not limited to, garlic; amino acids and various vitamins.

If the coating is to release in the colon, the film is based on shellac that dissolves above pH 7.4. If the coating is to meet the USP enteric release, the film will be based on a shellac that has an acid number of 81 or higher. Shellac resin is compatible with hydroxypropyl methylcellulose (HPMC), methylcellulose (MC), hydroxypropylcellulose (HPC), polyvinyl pyrrolidone (PVP), modified starch or maltodextrins and a variety of natural gums (acacia, etc.). These water soluble resins and any water soluble plasticizer can be formulated with shellac to give a film with the desired release characteristics. The plasticizers used may be glycerine, propylene glycol, polyethylene glycol (300–8000 MW), triacetin (TA), and triethyl citrate.

Also, plasticizers that are not soluble in water can be used in formulating. shellac systems. These plasticizers include castor oil, vegetable oils (corn, soy, etc.), acetylated monoglycerides, fatty acids, glyceryl monostearate and other glycerides and glycolates of fatty acids. When these plasticizers are used the coating solution is cloudy and requires stirring. Some materials derived from fatty acids can be ethoxylated to produce soluble plasticizers like polysorbate 80 which is very compatible with the shellac systems.

The resin systems formulated with HPMC and shellac have release characteristics surprisingly similar to straight shellac. However the coating process is easier to manage and produces an elegant film. MC slightly delays the release rate and PVP slightly increases the release rate compared to HPMC but most of the water soluble resins have little effect on the release rate, while improving the coating quality.

The flexibility of shellac to receive the large variety of additives listed gives rise to systems that can be formulated for precise pH release or to vary the rate of release at different pH values. The water based shellacs of various acid number give a starting composition of surprising versatility. Reliable and stable coatings are produced.

It is also to be noted that these systems can be formulated to receive any of the colors approved for use on foods and drugs. The incorporation of dyes and pigments can be tolerated to 50% of the resin level. There is no limit to lower quantity of color added but is determined by the desired color depth. Talc is also very compatible with the shellac systems.

The colors approved for use in foods and drugs may be any FDA approved colors, these include FD&C dyes and lakes, D&C dyes and lakes, titanium dioxide, iron oxide, natural colors and other materials such as talc, calcium carbonate and alumina. These colors may have some effect on the permeation of the film, but do not interfere with the release as controlled by the acid number of the shellac.

Based on shellac of varying acid number many formulations can be prepared to release at precise rates and pH. HPMC and most soluble resins and water soluble plasticizers have little effect on release but improve coating. MC slightly delays release and PVP slightly speeds up release. Oleic acid and other fatty acids improve coating and slightly lower the pH for release. Plasticizers insoluble in water like glyceryl monostearate slow the release slightly but improve the coating.

The following examples illustrate but do not limit the applications of this invention:

In the formulations presented the shellac entry will be designated with average acid number immediately following. The formulations will be presented as systems that are 15% solids. They may be diluted by the addition of water or concentrated by the elimination of water. If a particle is to be coated to a 15% weight gain, a 20% or higher concentration may be desirable for the coating system. Shellac systems are easily formulated for any of these applications. The percentages listed in the examples are by weight.

EXAMPLE 1

| | |
|---|---|
| Shellac 70 | 13.5% |
| Triacetin | 1.5% |
| Water | 85.0% |

This system of Example 1 has been coated on pellets of caffeine and vitamin C at 10–20% weight gain in a fluid bed coater and delays release of the active for 1–3 hours. Shellac with low acid number gives an excellent film that resists moisture permeation and gives good taste masking as well as delays release. This film will dissolve at pH above 7.5. Granules and powder of 100 mesh size can also be coated. These may be granules of various substances such as vitamin C, caffeine and other nutritional ingredients.

EXAMPLE 2

| | |
|---|---|
| Shellac 78 | 10.0% |
| HPMC | 2.5% or (3%) |
| Triacetin (TA) | 2.5% or (2%) |
| Water | 85.0% |

The combination of ingredients of Example 2 gives a fast release rate at pH 7.2 on garlic tablets when coated at 3–6% weight gain. Other dosage forms including large pellets, tablets, capsules and soft gels are readily coated in side vented coating pans, as well as the garlic. The percentages listed in the first column are presently preferred, although alternate percentages are listed in parentheses. Modified starch and maltodextrin may be used as a supplemental resin in Examples 1 or 2. Shellac 78 is not as good a film former as shellac 70 and may not tolerate them as well.

Enteric release can be accomplished using shellac with an acid number higher than 80. The USP 24 requires that a coated tablet resist gastric fluid of pH 1.2 for one hour in a standard disintegration apparatus and be completely gone from the basket in one hour in intestinal fluid of pH 6.8. The formula of Example 3 has been successfully used to enteric coat garlic.

EXAMPLE 3

| | |
|---|---|
| Shellac 83 | 10.0% |
| HPMC | 2.5% |
| Oleic acid | 1.9% |
| Propylene glycol | 0.6% |
| Water | 85.0% |

The system of Example 3 is applied at 34.0% weight gain on the garlic tablets. In intestinal fluid at pH 6.8 the film opens in less than 30 minutes. This film resists the gastric fluid for at least one hour.

EXAMPLE 4

| | |
|---|---|
| Shellac 78 | 10.0% |
| HPMC | 2.5% |
| Oleic acid | 1.9% |
| Triacetin | 0.6% |
| Water | 85.0% |

The formula of Example 4 also produces an enteric film. However, this film will not open at pH 6.8 in one hour. At a pH of 7.0 this film opens in less than 30 minutes.

EXAMPLE 5

| | |
|---|---|
| Shellac 78 | 9.4% |
| HPMC | 3.1% |
| Oleic acid | 1.9% |
| Polyethylene glycol 400 | 0.6% |
| Water | 85.0% |

The formula of Example 5 also produces an enteric film. But this film will not open at pH 6.8 in one hour. At a pH of 7.0 it opens in less than 30 minutes. This work is directed to produce films that dissolve without reference to the disintegration of the tablet which is dependent on the formulation of each unique dosage form.

Although the acid number of the shellac is used to select and control the pH at which the coating dissolves or releases, other components in the resin system may have some effect on the speed of the release. For example, glyceryl monostearate slows down the release whereas oleic acid speeds up the release. In other words, when oleic acid is present, the film coating will dissolve faster at that pH, therefore moving up slightly in the intestine where the coating will dissolve, as generally it is more acidic higher up in the intestinal track. This is also illustrated in Example 5 verses Example 6 wherein although both examples use shellac 78, the presence of oleic acid in Example 5 produces a release at pH of 7.0 as contrasted to a release at pH 7.2 in Example 6, which contains no oleic acid.

Examples 6 and 7 will illustrate the precise control of film dissolution which can be achieved with this invention.,

EXAMPLE 6

| | |
|---|---|
| Shellac 78 | 10.0% |
| HPMC | 2.5% |
| Triacetin | 2.5% |
| Water | 85.0% |

This film dissolves at a pH of 7.2

EXAMPLE 7

| | |
|---|---|
| Shellac 78 | 10.5% |
| HPMC | 3.0% |
| Oleic acid | 1.5% |
| Water | 85.0% |

This film dissolves at pH 7.0.

Oleic acid is an excellent plasticizer for this system, not only does it assist in forming a film of high quality, but it lowers the pH at which it dissolves. Oleic acid also has a tendency to increase the barrier to moisture migration into the tablet. Blends of fatty acids (C8–C18) have the same effect.

EXAMPLE 8

| | |
|---|---|
| Shellac 70 | 8.3% |
| HPMC | 4.2% |
| Oleic acid | 1.9% |
| Triacetin | 0.6% |
| Water | 85.0% |

The formula of Example 8 produces a film that gives colonic release. This film releases at pH 7.5 which is encountered in the colon.

Many examples have used a ratio of 4/1 for shellac/HPMC. This formula coats well but does not limit the shellac to HPMC ratio. The ratio of Shellac to HPMC has been varied from 2/1 to 15/1 with good success in enteric coatings. The preferred ratio is 3/1. The addition of HPMC is the preferred formulation for modifying shellac. HPMC is very compatible with shellac and prevents crosslinking and produces a system which coats with ease.

Oleic acid is an excellent plasticizer for this system because it detackifies the film and resists dissolving in the gastric fluid and speeds release in the intestinal fluids. The combination of HPMC and oleic acid is the preferred formulation for enteric and colonic release. PVP may replace HPMC in these formulations but the film is much more susceptible to moisture permeation and thicker films must be deposited to resist the gastric fluid. PVP is more useful when an immediate release film is desired because it also speeds up release in the intestinal fluid.

EXAMPLE 9

| | |
|---|---|
| Shellac 83 | 11.1% or (11.4%) |
| HPMC | 1.4% or (1.1%) |
| Oleic | 1.9% |
| Triacetin | 0.6% |
| Water | 85.0% |

The formulation of Example 9 releases quickly in intestinal fluid of pH 6.8. The percentages listed in the first column are presently preferred, although alternate percentages are listed in parentheses. If the HPMC is eliminated the system will continue to release at a pH 6.8. However the inclusion of HPMC with shellac is surprisingly efficacious. The film forms better with respect to elegance and barrier properties. Most surprising is the retention of enteric release because HPMC is so water soluble.

EXAMPLE 10

| | |
|---|---|
| Shellac 75 | 10.0% |
| HPMC | 2.5% |
| Oleic acid | 1.9% |

-continued

| | |
|---|---|
| Triacetin | 0.6% |
| Water | 85.0% |

The formulation of Example 10 releases at a pH 7.2. When a slower release is desired shellac of lower acid number can accomplish the result with precision. Some intestines may never reach the of pH 7.5 and this formula would give colonic release in such cases.

EXAMPLE 11

| | |
|---|---|
| Shellac 81 | 10.0% |
| HPMC | 2.5% |
| Oleic acid | 1.9% |
| Propylene glycol | 0.6% |
| Water | 85.0% |

The formulation of Example 11 releases at a pH of 6.8 in a short time.

All of these shellac systems can be colored with the standard approved color additives which includes titanium dioxide, iron oxides, FD&C lakes and dyes, and D&C lakes and dyes. Talc and natural colors such as carmine, annato, turmeric, Beta carotene, riboflavin, etc. can be used to color shellac systems.

EXAMPLE 12

| | |
|---|---|
| Shellac 85 | 9.4% |
| HPMC | 3.1% |
| Glyceryl Monostearate | 1.25% |
| Triethyl Citrate | 1.25% |
| Titanium dioxide | 5.0% |
| Water | 80.0% |

The formulation of Example 12 is 20% solids but can easily be sprayed on tablets and gives a slow release at pH 6.8. Little influence on the release characteristics is noted from the colors.

These unique shellac formulations provide a useful series of coating properties that offer specific release characteristics for tablet coating. These systems have shown good stability in storage which also is surprising for shellac.

Other examples of controlled release films in accordance with the present invention include the following Examples 13 through 17. In each of these examples, the percentage of water content is not listed, but it is understood that it makes up the balance.

A film coating that produces a controlled release in an environment having a pH of about 7.4 may be based on the use of a shellac with an acid number of 70. This may preferably be modified with HPMC at about 33% of the shellac and plasticized with triacetin at about 15% of the total resin. This is illustrated in the following Example 13.

EXAMPLE 13

| | |
|---|---|
| Shellac 70 | 9% |
| HPMC | 3% |
| Triacetin | 3% |

Another example of a controlled release film is one that releases at a pH of about 7.0 based on a shellac with an acid number of about 83, MC at 25% of the shellac, oleic acid making up 15% and propylene glycol at about 5% of the total resin. An example of this is set forth in Example 14.

EXAMPLE 14

| | |
|---|---|
| Shellac 83 | 10% |
| MC | 2.5% |
| Oleic acid | 1.9% |
| Propylene glycol | .6% |

Another example of a film that produces a controlled release is one that releases in an environment having a pH of about 6.7 which utilized shellac having an acid number of about 85 with HPMC at about 33% of the shellac and with glyceryl monostearate and triethyl citrate each at about 10% of the total resin. An example of this is set forth in Example 15.

EXAMPLE 15

| | |
|---|---|
| Shellac 85 | 10% |
| HPMC | 2.5% |
| Glyceryl monostearate | 1.3% |
| Triethyl citrate | 1.3% |

Another example of a film with a Controlled release which releases in an environment having a pH of about 6.7 utilizes a shellac with an acid number of about 85.7 with HPMC at about 33% of the shellac and glyceryl monostearate and triethyl citrate each at about 10% of the total resin. Titanium dioxide may be added to this film at up to about 50% of the total resin. An example is set forth in Example 16.

EXAMPLE 16

| | |
|---|---|
| Shellac 85.7 | 9.3% |
| HPMC | 3.1% |
| Glyceryl monostearate | 1.3% |
| Triethyl citrate | 1.3% |

In view of the above, the present invention may be embodied in other specific forms without departing from the spirit or essential attributes thereof and, accordingly, reference should be made to the appended claims, rather than to the foregoing specification as indicating the scope of the invention.

I claim:

1. A coating composition for forming a film coating suitable for use on pharmaceuticals and foods, comprising: a composition including a shellac of a preselected acid number to provide a controlled release profile in an environment of a predetermined pH, wherein the shellac is selected to have an acid number above 80 to provide film release or dissolution in an environment having a pH below 7.0; and being comprised of shellac having an acid number in the range of 80 to 91, HPMC at 10 to 50% of the shellac, fatty acid at 10 to 20% of the total resin and triacetin at 5 to 10% of the total resin.

2. A coating composition for forming a film coating suitable for use on pharmaceuticals and foods, comprising:

a composition including a shellac of a preselected acid number to provide a controlled release profile in an environment of a predetermined pH, wherein the shellac is selected to have an acid number above 80 to provide film release or dissolution in an environment having a pH below 7.0; and which releases in an environment having a pH of about 6.8, being comprised of shellac with an acid number of about 81, HPMC at about 25% of the shellac, oleic acid at approximately 13% of the total resin and propylene glycol at approximately 4% of the resin.

3. A coating composition for forming a film coating suitable for use on pharmaceuticals and foods, comprising:

a composition including a shellac of a preselected acid number to provide a controlled release profile in an environment of a predetermined pH, wherein the shellac is selected to have an acid number above 80 to provide film release or dissolution in an environment having a pH below 7.0; and which releases in an environment having a pH of about 6.8, being comprised of shellac with an acid number of about 83, HPMC at about 25% of the shellac, oleic acid at about 13% of the total resin and propylene glycol at about 4% of the resin.

4. A coating composition for forming a film coating suitable for use on pharmaceuticals and foods, comprising:

a composition including a shellac of a preselected acid number to provide a controlled release profile in an environment of a predetermined pH, wherein the shellac is selected to have an acid number above 80 to provide film release or dissolution in an environment having a pH below 7.0; and which releases in an environment having a pH of about 7.0, being comprised of shellac with an acid number of about 83, methylcellulose at about 25% of the shellac, oleic acid at about 13% of the total resin and propylene glycol at about 4% of the total resin.

5. A coating composition for forming a film coating suitable for use on pharmaceuticals and foods, comprising:

a composition including a shellac of a preselected acid number to provide a controlled release profile in an environment of a predetermined pH, wherein the shellac is selected to have an acid number above 80 to provide film release or dissolution in an environment having a pH below 7.0; and which releases in an environment having a pH of about 6.7, being comprised of shellac having an acid number of about 85, HPMC at about 25% of the shellac, glyceryl monostearate at about 10% of the total resin and triethyl citrate at about 10% of the resin.

6. A coating composition for forming a film coating suitable for use on pharmaceuticals and foods, comprising:

a composition including a shellac of a preselected acid number to provide a controlled release profile in an environment of a predetermined pH, wherein the shellac is selected to have an acid number above 80 to provide film release or dissolution in an environment having a pH below 7.0; and which releases in an environment having a pH of about 6.7, being comprised of shellac with an acid number of about 85.7, HPMC at about 33% of the shellac, glyceryl monostearate at 9% of the total resin, triethyl citrate at 9% of the resin and titanium dioxide at up to 50% of the resin.

7. An enteric coating composition comprised of:

shellac with an acid number from about 81 to about 83;

HPMC at about 25% of the shellac by weight;

oleic acid at approximately, 13% of the total resin; and propylene glycol at approximately 4% of the resin;

wherein said enteric coating composition at least partially dissolves or releases in an environment having a pH of about 6.8.

* * * * *

UNITED STATES PATENT AND TRADEMARK OFFICE
CERTIFICATE OF CORRECTION

PATENT NO.    : 6,620,431 B1
DATED         : September 16, 2003
INVENTOR(S)   : Signorino It is certified that error appears in the above-identified patent and that said Letters Patent is hereby corrected as shown below:

Column 1,
Line 37, delete "erased" and substitute therefor -- water based --.

Column2,
Line 47, insert a space after "74-80" and before "dissolves".
Line 66, delete "." after "compositions".
Line 67, delete ";" and substitute therefor -- , --.

Column 3,
Line 15, delete "." after "formulating".

Column 10,
Line 36, delete "," after "approximately".

Signed and Sealed this

Twenty-first Day of October, 2003

JAMES E. ROGAN
*Director of the United States Patent and Trademark Office*